United States Patent [19]
Kontos

[11] Patent Number: 6,048,357
[45] Date of Patent: Apr. 11, 2000

[54] ANCHORING DEVICE AND METHOD FOR SEALING PUNCTURES IN VESSELS

[75] Inventor: Stavros Kontos, Woodcliff Lake, N.J.

[73] Assignee: x-Site, L.L.C., Totowa, N.J.

[21] Appl. No.: 09/112,234

[22] Filed: Jul. 9, 1998

[51] Int. Cl.[7] .................................................. A61B 17/00
[52] U.S. Cl. ............................................................ 606/213
[58] Field of Search .................................. 606/213, 215, 606/212; 604/104, 106, 107, 174, 177; 128/898, 899

[56] References Cited

U.S. PATENT DOCUMENTS

| | | | |
|---|---|---|---|
| 4,961,741 | 10/1990 | Hayhurst | 606/139 |
| 5,133,723 | 7/1992 | Li et al. | 606/148 |
| 5,324,298 | 6/1994 | Phillips et al. | 606/148 |
| 5,439,470 | 8/1995 | Li | 606/148 |
| 5,496,332 | 3/1996 | Sierra et al. | 606/213 |
| 5,527,322 | 6/1996 | Klein et al. | 606/144 |
| 5,613,974 | 3/1997 | Andreas et al. | 606/144 |
| 5,728,122 | 3/1998 | Leschinsky et al. | 606/213 |
| 5,746,755 | 5/1998 | Wood et al. | 606/148 |
| 5,779,719 | 7/1998 | Klein et al. | 606/144 |
| 5,792,152 | 8/1998 | Klein et al. | 606/144 |

*Primary Examiner*—Michael Buiz
*Assistant Examiner*—Vikki Trinh
*Attorney, Agent, or Firm*—Kenyon & Kenyon

[57] ABSTRACT

A device for sealing a puncture in a tissue within a living body, comprises a flexible tube including an opening, wherein the flexible tube extends from a proximal end which, when the device is in an operative position, is located outside the living body, to a distal end which, in the operative position, is located within the living body on a distal side of the puncture in combination with an inner member received within the flexible tube so that the inner member may move proximally and distally with respect to the flexible tube. A first end of a flexible anchor member is coupled to the inner member so that, when the inner member is moved with respect to the outer member, a second end of the anchor member extends through the opening outside the flexible tube. An adhesive may be applied via an adhesive lumen to seal the puncture.

26 Claims, 19 Drawing Sheets

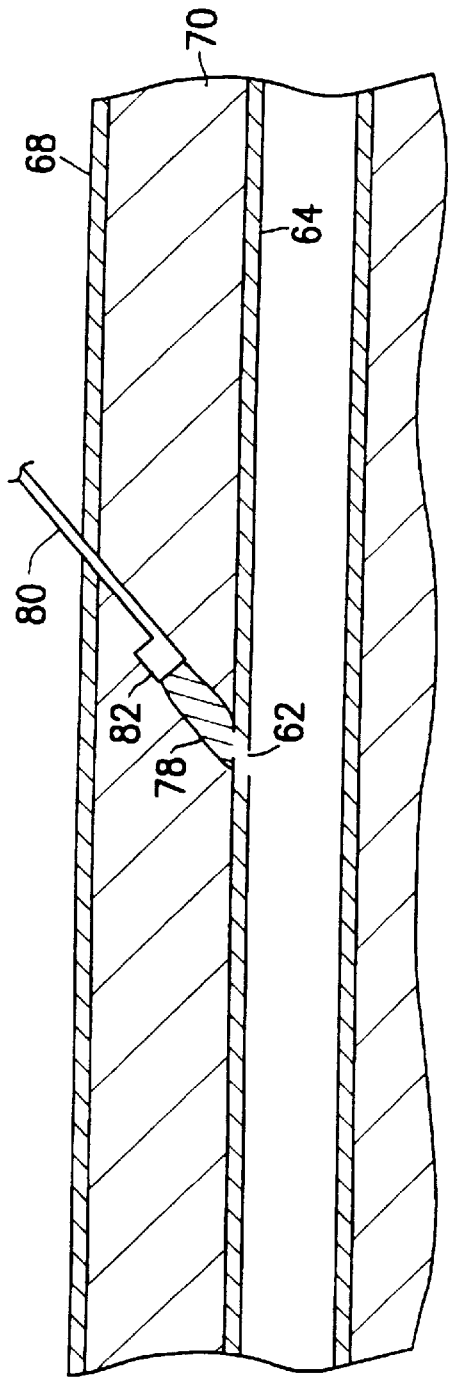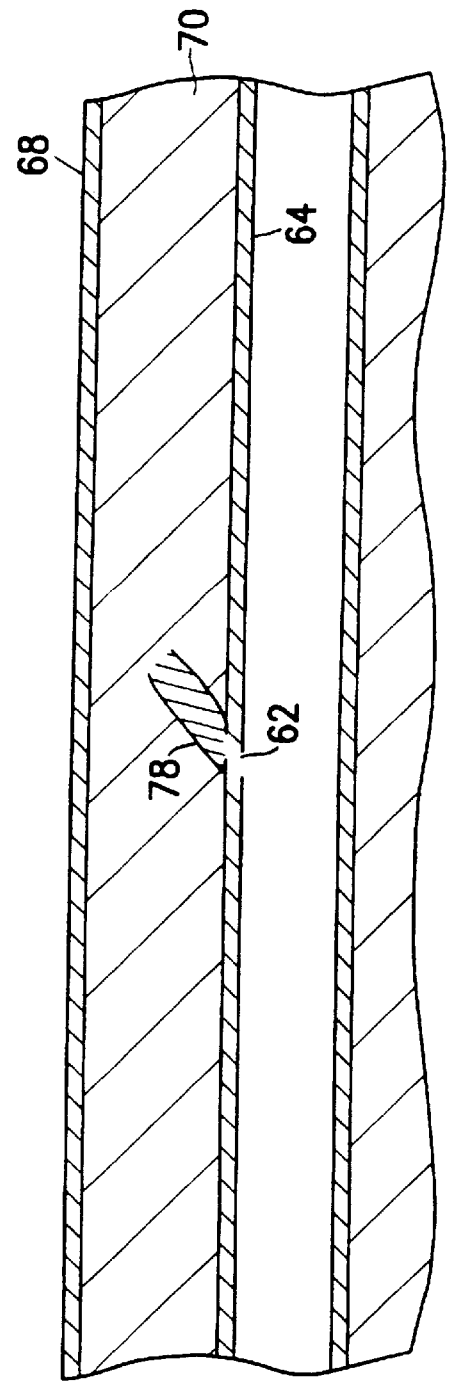

ANCHORING DEVICE AND METHOD FOR SEALING PUNCTURES IN VESSELS

FIELD OF THE INVENTION

This invention relates generally to medical devices and more particularly to devices for sealing percutaneous formed punctures or incisions in blood vessels created during a catheterization procedure such as are common in angioplasty and angiography.

BACKGROUND OF THE INVENTION

Typically, a Cardiologist, or Invasive Cardiologist performing an intravascular procedure first uses a needle to create a percutaneous puncture into the artery. A guide-wire is then placed, via the needle, through the puncture site into the artery. The needle is withdrawn and a conventional percutaneous introducer sheath is placed over the guide-wire. The introducer sheath extends into the channel of the artery and serves as a means for medical instruments to be inserted and removed as necessary to perform the operative procedure. Once the operative procedure has been concluded and the medical instrument and introducer sheath are removed, it becomes necessary to stop bleeding at the puncture site. Note particularly that the size of the opening of the puncture may vary greatly depending upon the procedure being performed. For example, the opening can range from as little as 1.67 mm to 2.67 mm (5 to 8 French) for a standard angiography procedure to as much as 6.0 mm to 6.67 mm (18 to 20 French) for cardiopulmonary support systems. The opening may be further enlarged by prolonged manipulation of various catheters, sheaths and instruments entering and exiting the treatment site.

Conventional medical practice with respect to the closure issue has been to simply apply external manual pressure to the puncture site for as long as it takes for hemostasis or clotting to occur. While effective ultimately, the conventional practice suffers from a number of drawbacks. The length of time that pressure is required in order to induce clotting may run as long as 45 minutes in the case of punctures into femoral arteries, or even longer if the patient has been pre-treated with anticoagulant medication. At best, such prolonged external pressure results in pain, substantial post-operative bruising and extended recuperative stays; at worst, excessive pressure for an extended period of time can result in development of a pseudo-aneurysm or severe hematoma. Moreover, from the perspective of economic efficiency, this practice is viewed as a wasteful use of the precious time of physicians and other highly skilled medical personnel.

There have been relatively recent attempts made in the prior art to find alternate solutions to the puncture site closure problem. For example, Kensey in U.S. Pat. No. 4,890,612, describes a device comprising plug means, a holding portion to hold the plug means in place, and a sealing portion formed of foam hemostatic material. Unfortunately, this device leaves a foreign body in the arterial lumen, which body may dislodge and embolize the artery. In addition, Kensey fails to provide a means for positively locating the puncture site in the blood vessel.

Sinofsky, in U.S. Pat. No. 4,929,426, employs a semi-rigid tube having an inflatable balloon, which after proper positioning, is inflated to apply pressure directly to the outside of the arterial wall. Laser energy is then directed to the site, via an optical fiber in the tube, to thermally weld the artery and seal the puncture. This device suffers from being relatively expensive and overly complicated. In addition, as with Kensey, there is no means to positively locate the puncture site in the arterial wall.

Fowler, in U.S. Pat. Nos. 5,108,421 and 5,275,616, uses a balloon catheter, or alternatively a cylindrical insertion assembly having a proximal plunger member associated therewith, to position an implantable vessel plug into the puncture site, which plug is over time absorbed into the surrounding tissue. This device suffers the shortcoming that the vessel plug can slide along the side of the balloon catheter causing improper plug positioning. And, once again, there is no means to positively locate the puncture site.

Gershony et. al., in U.S. Pat. No. 5,383,896, provide a percutaneous sealing device with a shaft through which a balloon is inflated and withdrawn until the balloon hemostatically engages the inner surface of the blood vessel. Inflation pressure is then maintained until clotting seals the puncture site. But since both the vessel and the balloon are compliant, the device can easily be drawn through the puncture site, thus defeating the purpose. Nor is any means for positively locating the puncture site provided.

Klein et. al., in U.S. Pat. No. 5,417,699, resort to a suturing approach wherein needles and suture material are introduced into the lumen of a body structure via a narrow shaft, and configured in such a manner that when passed back through the tissue a loop of suture is left behind which, when tied, completes closure of the puncture site. Here again, absent means to positively locate the puncture site (and with no way to assure the device is properly centered), Klein's needles may not suture the artery at the appropriate spot.

SUMMARY OF THE INVENTION

The present invention is directed to a device for sealing a puncture in a tissue within a living body, including a flexible tube having an opening. The flexible tube extends from a proximal end at which a user grips the device to a distal end which, when the device is in an operative position, is located within the living body on a distal side of the puncture. An inner member, slidably received within the flexible tube so that the inner member may be moved proximally and distally with respect to the flexible tube, is coupled to a first end of a flexible anchor member so that, when the inner member is moved with respect to the outer member, a second end of the anchor member extends through the opening outside the flexible tube. A sealing device is included for temporarily preventing the flow of bodily fluids to the puncture during the use of the device.

An embodiment of the present invention also includes an axially-extending adhesive lumen disposed within the flexible tube, the adhesive lumen extending from an adhesive inlet port to an adhesive exit port. The adhesive exit port is arranged along the flexible tube so that the adhesive exit port is adjacent to the puncture when the device is in the operative position. With the flow of bodily fluids temporarily obstructed, for example, an adhesive may be applied through the adhesive lumen to seal the puncture in the vessel.

BRIEF DESCRIPTION of the DRAWINGS

FIG. 14 shows sealing material within the patient after the device has been withdrawn leaving only the plunger and the sealing material in the patient's body;

FIG. 15 shows the sealing material within the patient's body after the plunger has been withdrawn;

DETAILED DESCRIPTION

Figure 1:
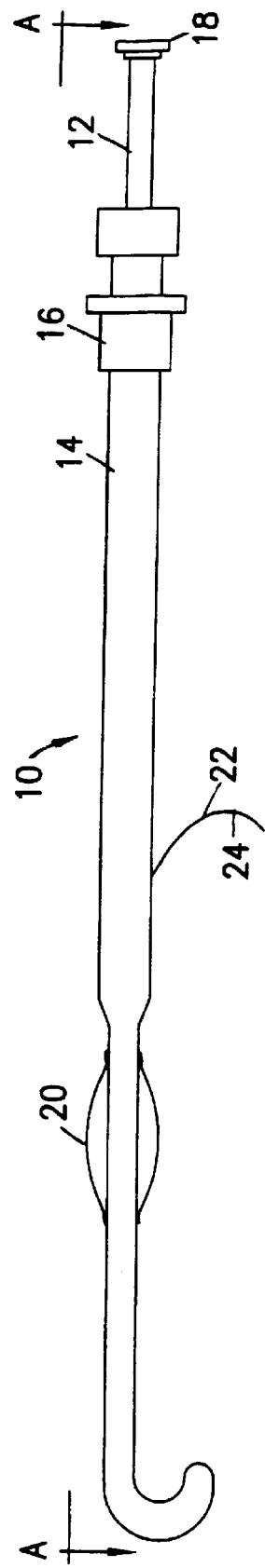
FIG. 1 is a plan view of a device according to the present invention.
Figure 2:
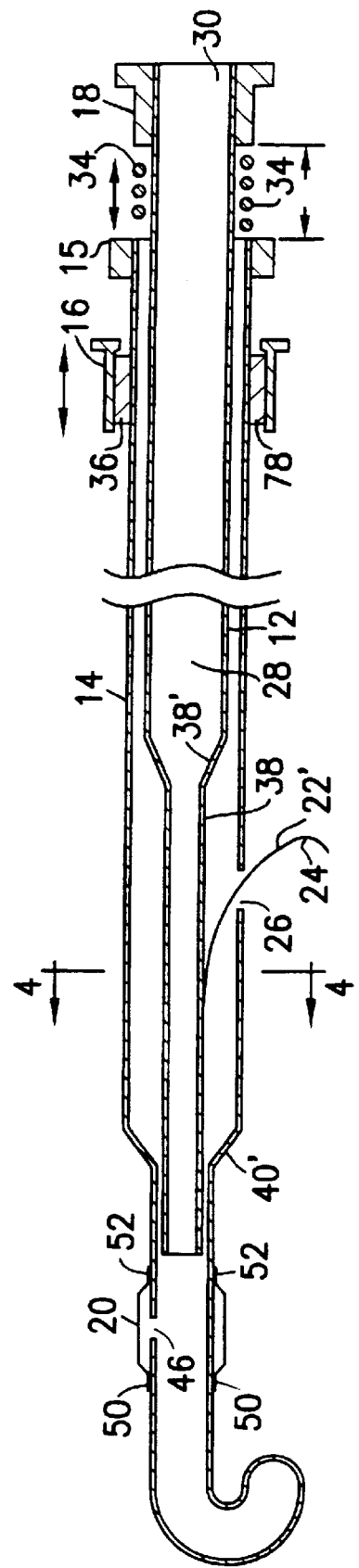
FIG. 2 is cross-sectional view taken along Line A—A of FIG. 1, showing a first single-lumen embodiment of the invention.
Figure 3:
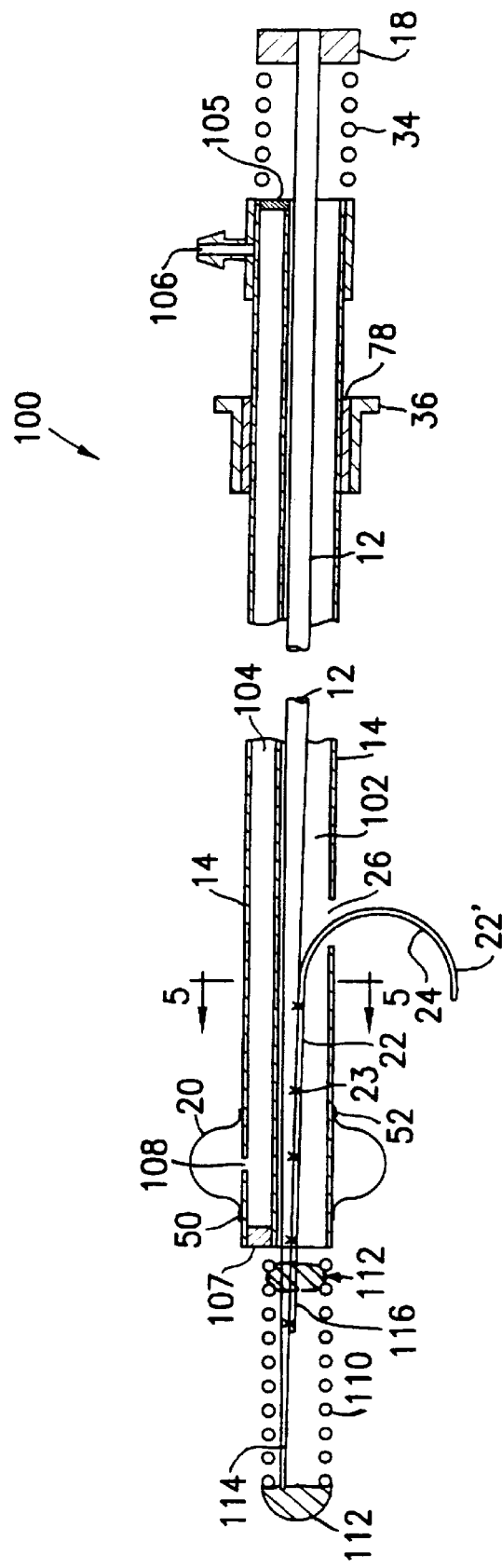
FIG. 3 is a cross-sectional view taken along Line A—A of FIG. 1, showing a second dual-lumen embodiment of the invention.

Referring now in greater detail to the various drawings wherein like reference numerals refer to like parts, and wherein reference to the proximal end of an element means the end nearest to the operator and the distal end of an element means the end furthest away from the operator there is shown generally at 10 in FIG. 1 a first embodiment of a device 10 for positively locating and sealing percutaneously formed punctures or incisions such as are common during catheterization procedures in angioplasty and angiography. The device 10, which may preferably be approximately 20" in length, comprises an inner tubular body 12 with a handle 18 formed at a proximal end thereof, slidably received within an outer tubular body 14 a proximal end of which forms a housing 16 for the storage of a hemostatic sealing material. The distal end of the outer tubular body 14 may optionally include an expandable member which functions as a blood vessel occluding device. As shown in FIG. 3, an occluding balloon 20 may perform this function. However, those skilled in the art will recognize that any of various selectively expandable sealing members may be employed to occlude the flow of blood through the blood vessel. As shown in FIG. 1, a resilient anchoring member 22, coupled to the distal end of the inner tubular body 12, is preferably biased so that, in an unstressed state the anchor member forms a curve 24 with an open end of the curve facing distally. As seen in FIG. 2, this curve may be substantially J-shaped. The anchoring member 22, which may be coupled to the inner tubular body 12 at welds 23, retracts and deploys through an opening 26 formed in the outer tubular body 14.

Figure 4:
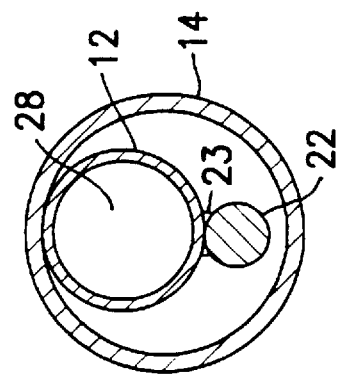
FIG. 4 is a cross-sectional view of the device of according to the first embodiment taken along line 4—4 of FIG. 2.

As shown in FIGS. 2 and 4, the inner tubular body 12 according to the first embodiment of the invention defines a lumen 28 or working channel whose proximal end includes a port 30 which may serve as the transmission pathway for inflation/deflation of the occluding balloon 20. The handle 18 is designed to cooperatively engage the proximal end 15 of outer tubular body 14 to prevent the advancement of the inner tubular body 12 proximally beyond a predetermined maximum distance. In addition, a compression spring 34 may optionally be included to assure that inner tubular body 12 is not accidentally advanced relative to the outer tubular body 14. As can be seen in FIGS. 2 and 3, when the inner tubular body 12 has been advanced distally with respect to the outer tubular body 14, the anchor member 22 is retracted through the opening 26 and, when the inner tubular body 12 is moved proximally with respect to the outer tubular body 14, a free end 22' of the anchor member 22 moves along an inner surface of the outer tubular body 14 until it reaches the opening 26. When the free end 22' reaches the opening 26, the bias of the anchor member 22 urges the free end 22' out through the opening 26 so that the anchor member 22 is deployed through the opening 26 and assumes its curved shape as seen in FIGS. 1 and 2.

With respect to the housing 16, also visible in FIG. 2 is an annular hemostatic sealing material holding chamber 36, which may be receive any suitable hemostatic sealing material 78 such as a sponge-like plug of collagen. The distal end of the inner tubular body 12 includes an inner reduced diameter, stepped down portion 38 approximately four inches (4") in length, which is designed to cooperatively engage with an outer reduced diameter, stepped down section 40 formed in the outer tubular body 14. The length of the space between the inner stepped down section 38 and the outer stepped down section 40 is preferably equivalent to, or slightly greater than, the predetermined maximum advancement distance of the inner tubular body 12 so that, when the inner tubular body 12 is advanced distally relative to the outer tubular body 12 as far as it may be, an abutting wall 38' of the inner tubular body 12 contacts an abutting wall 40' of the outer tubular body 14. The curve 24 of the retractable anchor 22 and the resilience of the material of which the anchor member 22 is made, which material may preferably be nitinol, cooperate such that as the inner tubular body 12 is advanced and retracted with respect to the outer tubular body 14, the anchoring member 22 retracts through and deploys from the opening 26 of outer tubular body 14.

The occluding balloon 20 (or other blood vessel occluding device) is preferably located about 1" in from the opening 26 of the device 10 as shown in FIG. 2. The occluding balloon 20, which may be inflated and deflated via receiving port 30 of the inner tubular body 12 and the port 46 formed in the outer tubular member 14, is fixedly secured to the outer tubular body 14 at seal points 50, 52.

Figure 5:
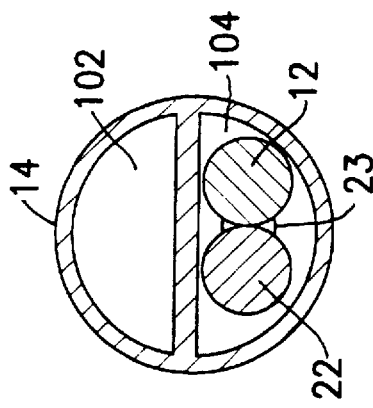
FIG. 5 is a cross-sectional view of the device according to the second embodiment taken along line 5—5 of FIG. 3.

As shown in FIGS. 3 and 5, a device 100 according to a second embodiment of the invention may comprise a dual lumen arrangement. The outer tubular body 14 of the device of FIG. 3 is split into a first lumen 102 of substantially semi-circular cross-section located substantially adjacent and parallel to a second lumen 104 also of substantially semi-circular cross-section. The second lumen 104 serves as a dedicated channel for inflation/deflation of the occluding balloon 20 and includes seals 105 and 107 at proximal and distal ends, respectively. Specifically, a first port 106, communicating with the second lumen 104, is formed in a proximal end of the outer tubular body 14 and air introduced into the second lumen via the port 106 travels along the second lumen to a distal opening 108 from which it flows into the occluding balloon 20. The inner tubular body 12, which need not include an interior lumen 28, and the anchor member 22 are received within the first lumen 102. The distal end of the device 100 may include a flexible spring 110 biased so that it assumes a "J-shape" when unstressed. The spring 110 may be coupled to distal portions 114 and 116, respectively, of the inner tubular member 12 and the anchor member 22 which project out of the distal end of the first lumen 102 by means of welds 112.

Figure 6:
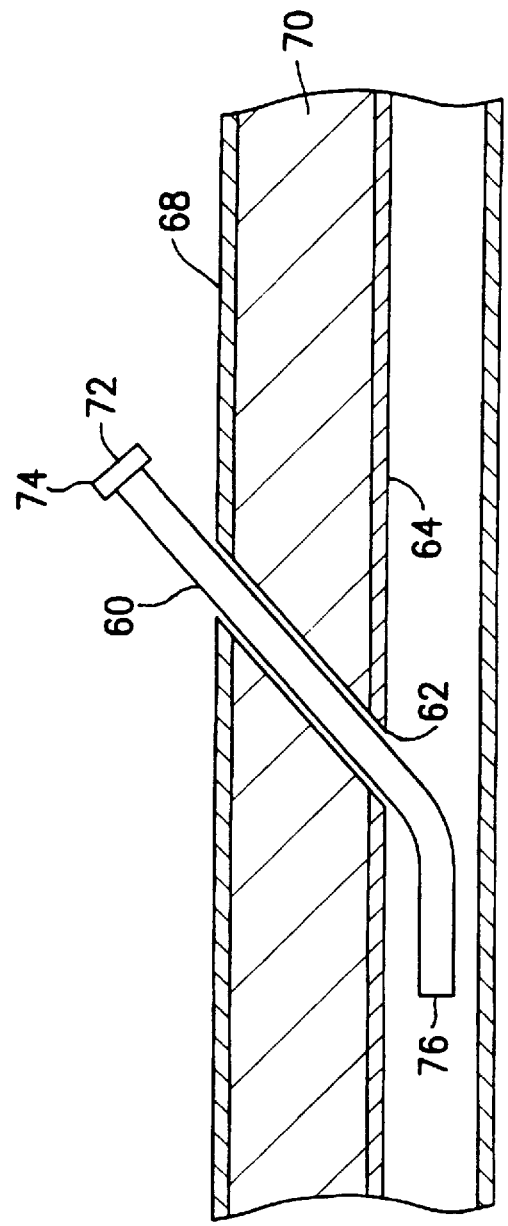
FIG. 6 is a side elevational view showing the positioning of the percutaneous introducer sheath within the body of the patient.

FIGS. 6–15 show a series of side elevational views illustrating the use of the device 100. FIG. 6 shows the percutaneous introducer sheath 60, which is approximately 6" in length, in place penetrating through the patient's skin 68 and underlying fascia 70, through the puncture site 62 of the arterial wall 64 into the interior of the arterial lumen 66. Access through the introducer sheath 60 is via a valve 72 located at the proximal tip 74 thereof, and an interior channel of the introducer sheath 60 continues to the distal tip 76 thereof.

Figure 7:
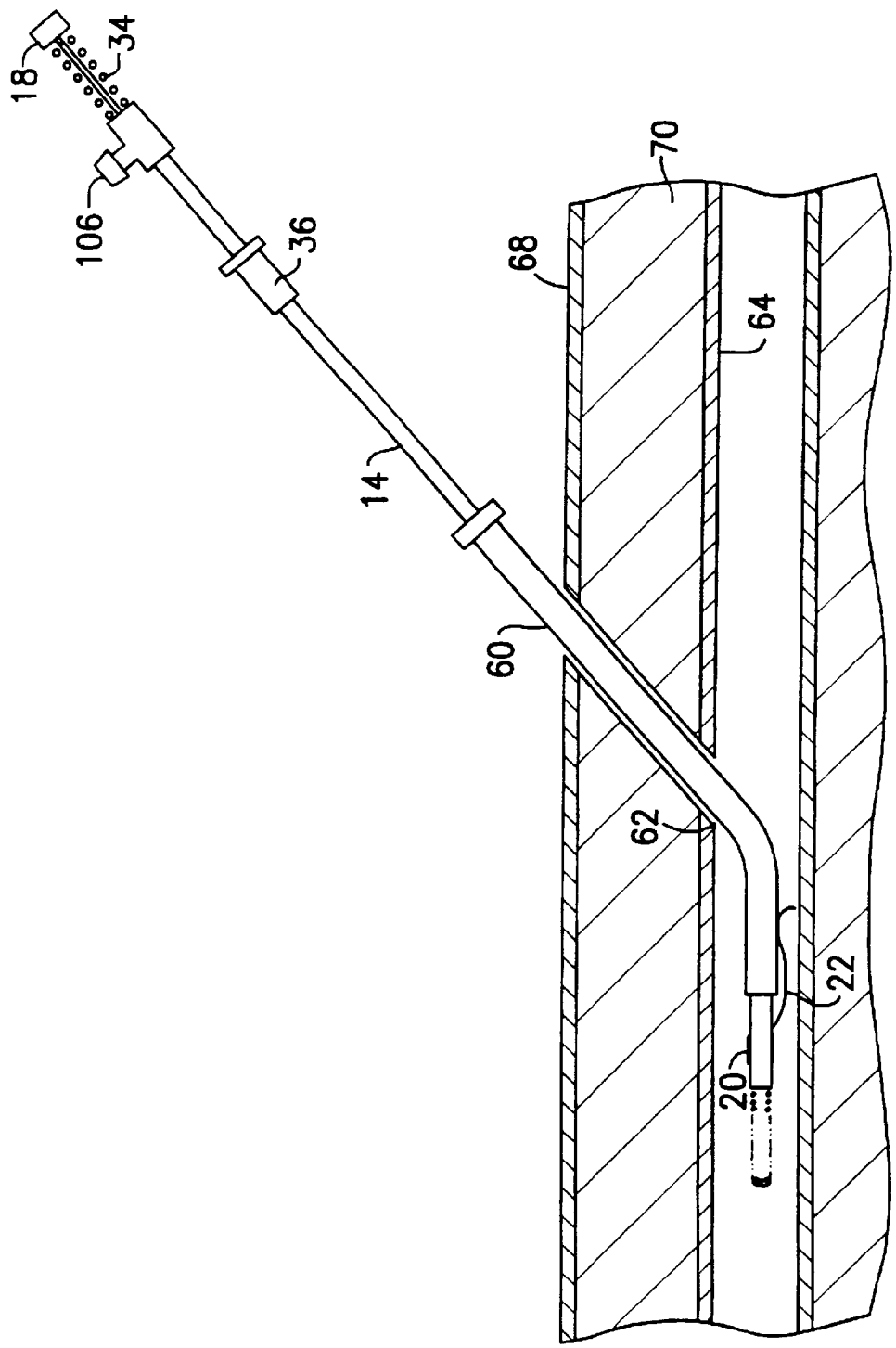
FIG. 7 is a side elevational view of the device according to the second embodiment of the instant invention, showing the device inserted into the introducer sheath with the occluding balloon deflated.
Figure 8:
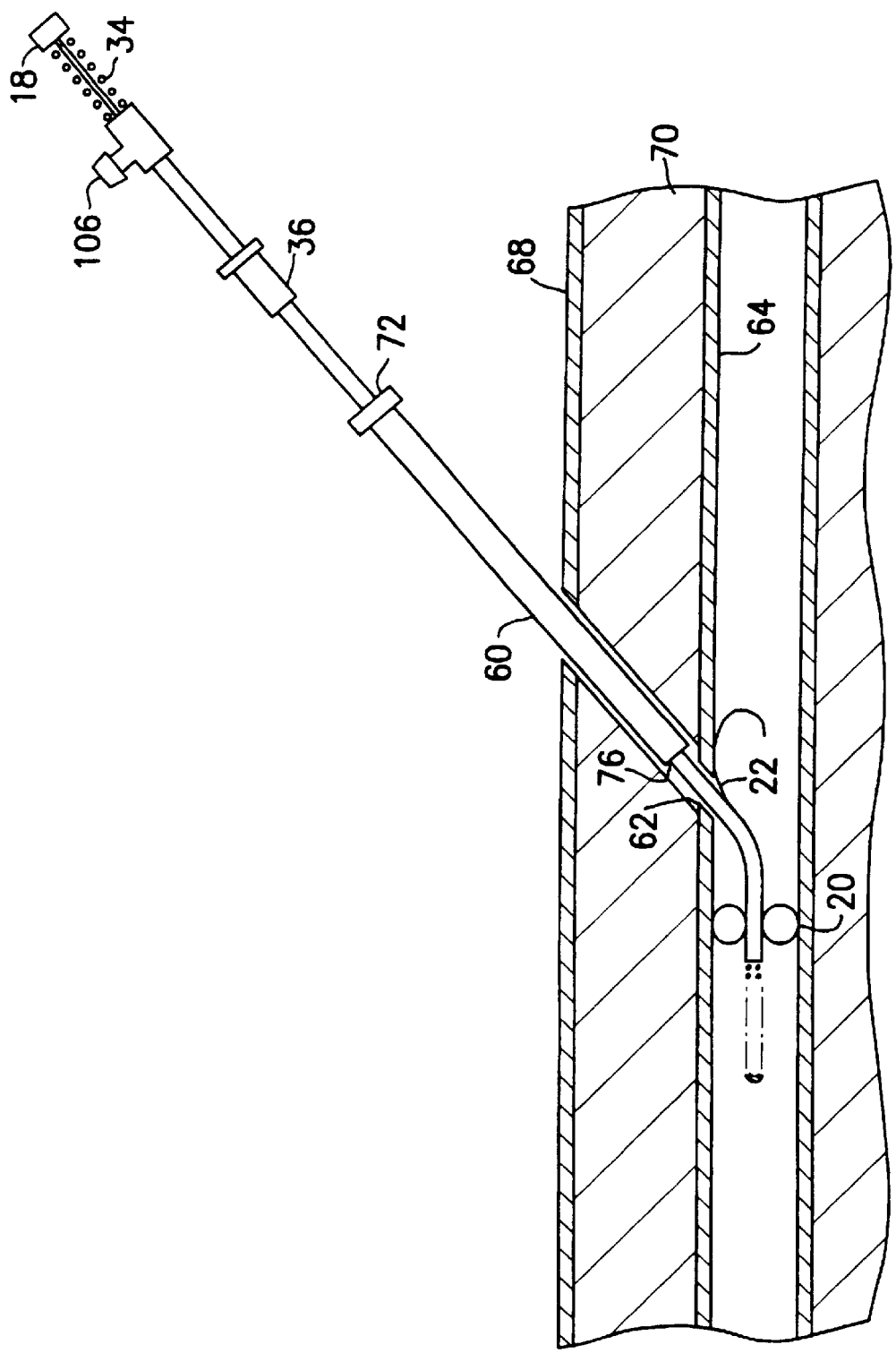
FIG. 8 is a side elevational view of the device according to the second embodiment of the instant invention, showing the anchor wire engaged with the inner portion of the arterial wall of the puncture site.

As can be seen in FIG. 7, the device 100, with the anchor member 22 preferably in the retracted position, is inserted through the introducer sheath 60 until its distal end passes to a point approximately 2" beyond the distal tip 76 of the introducer sheath 60. Thereafter, the inner tubular body 12 is moved proximally relative to the outer tubular body 14 to deploy the anchor member 22 so that it assumes its curved shape and extends outside of the outer tubular body 14. The device 100 is then retracted proximally until the anchoring member 22 engages the distal tip 76 of the introducer sheath 60 and the occluding balloon 20 is inflated as shown in FIG. 8.

Figure 9:
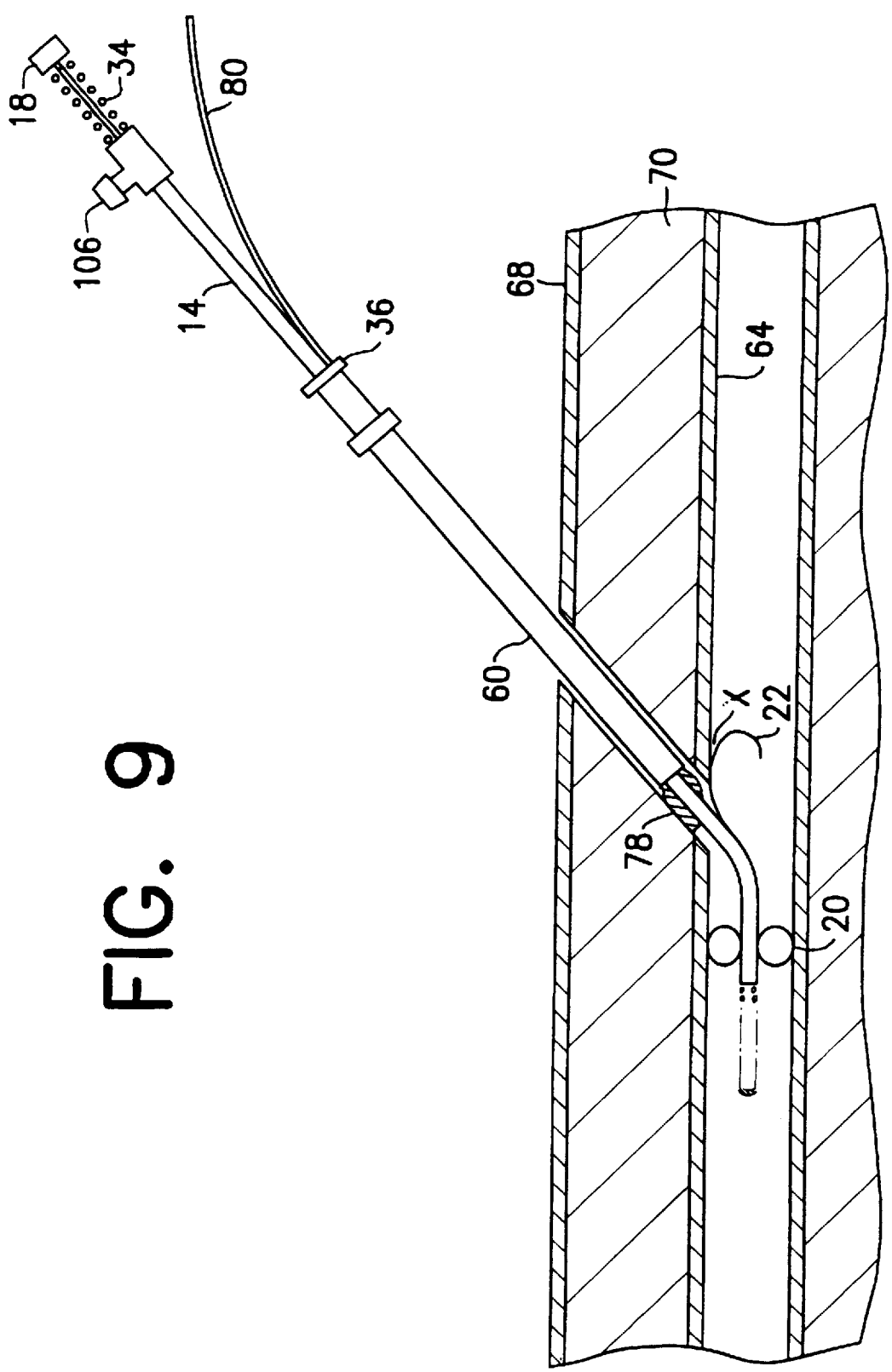
FIG. 9 is a side elevational view of the device according to the first embodiment of the invention in a position wherein sealing material is being inserted toward the puncture site.

Once the occluding balloon 20 has been inflated, the device 100 and the introducer sheath 60 are retracted approximately one and one half inches (1.5"), to a point where the anchoring member 22 engages the arterial wall 64 as shown in FIG. 9, more specifically, the J-bend 24 abuts against an interior portion of the arterial wall 64 at a point "X" adjacent to the puncture site 62.

Figure 10:
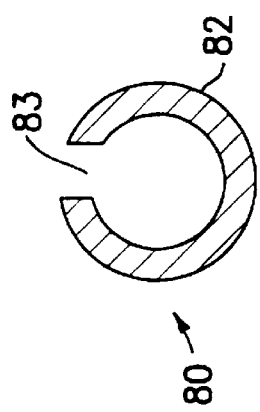
FIG. 10 is a front view of a plunger for use with a device according to the present invention.
Figure 11:
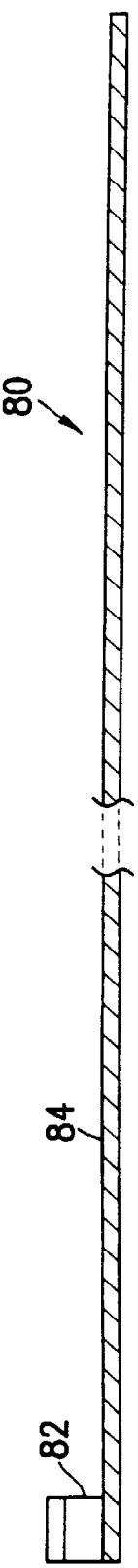
FIG. 11 is a side view of the plunger of FIG. 11.

Having now positively located the puncture site 62 and positively anchored the device 100, the hemostatic sealing material 78 is moved from the holding chamber 36 through the introducer sheath 60 to the distal tip 76 thereof, via insertion into the introducer sheath 60, through the holding chamber 36, of a plunger 80. As shown in FIGS. 10 and 11, the plunger 80 may preferably include a substantially circular distal end 82 having a slot 83 which may be slidably received around the outer tubular body 14. A proximally protruding member 84 is employed by the doctor to move the plunger 80 distally through the hemostatic material holding chamber 36 and along the outer tubular body 14 to advance the hemostatic sealing material 78 to the puncture site. FIG. 9 depicts the device 100 wherein part of the housing 16 and the holding chamber 36 have been advanced through the valve 72 into the sheath 60, and the plunger 80 has pushed the hemostatic sealing material 78 downward through the introducer sheath 60 to the puncture site 62.

Figure 12:
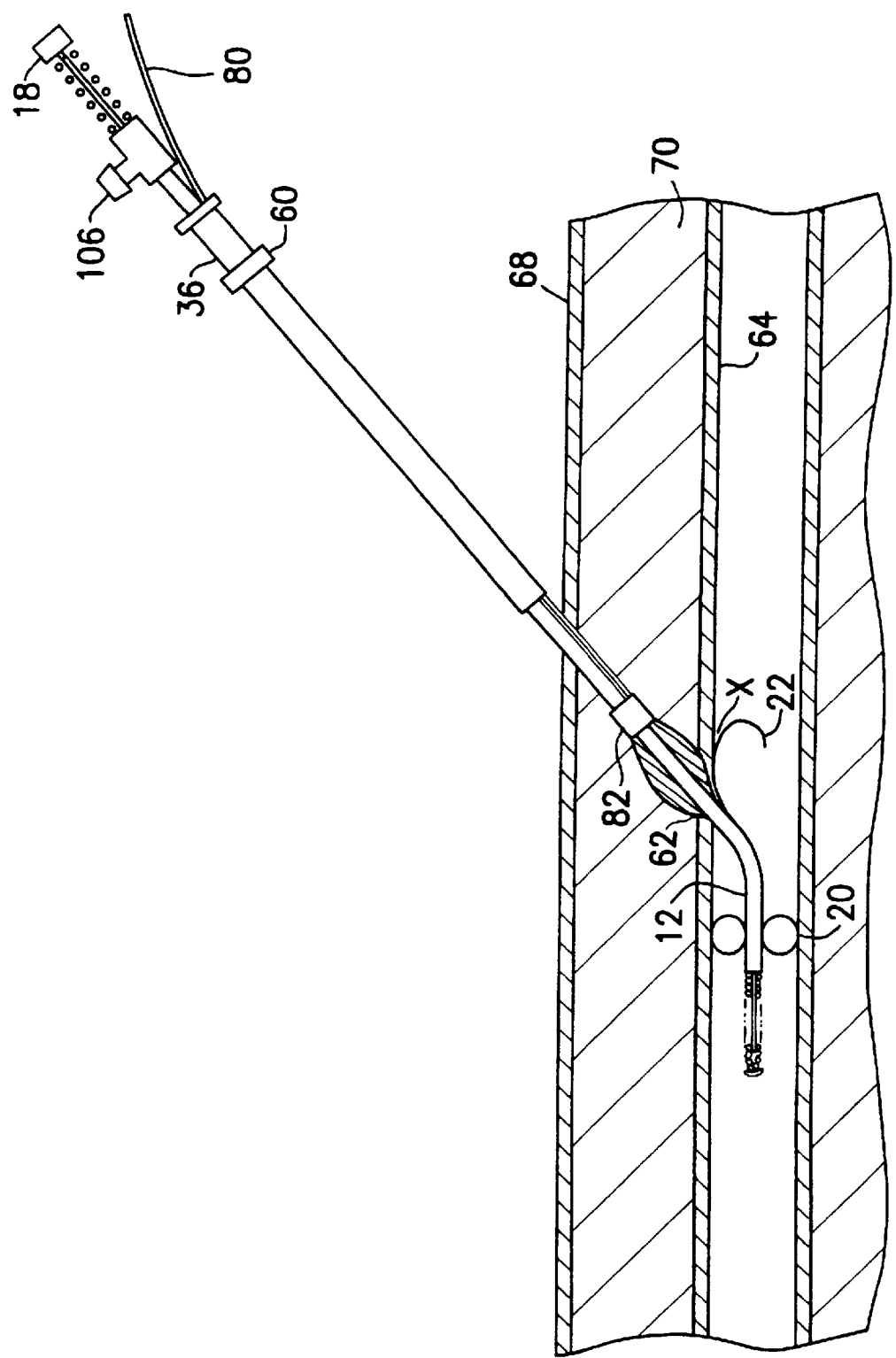
FIG. 12 is a side elevational view of the device according to the second embodiment of the invention in a position wherein the introducer sheath has been withdrawn.
Figure 13:
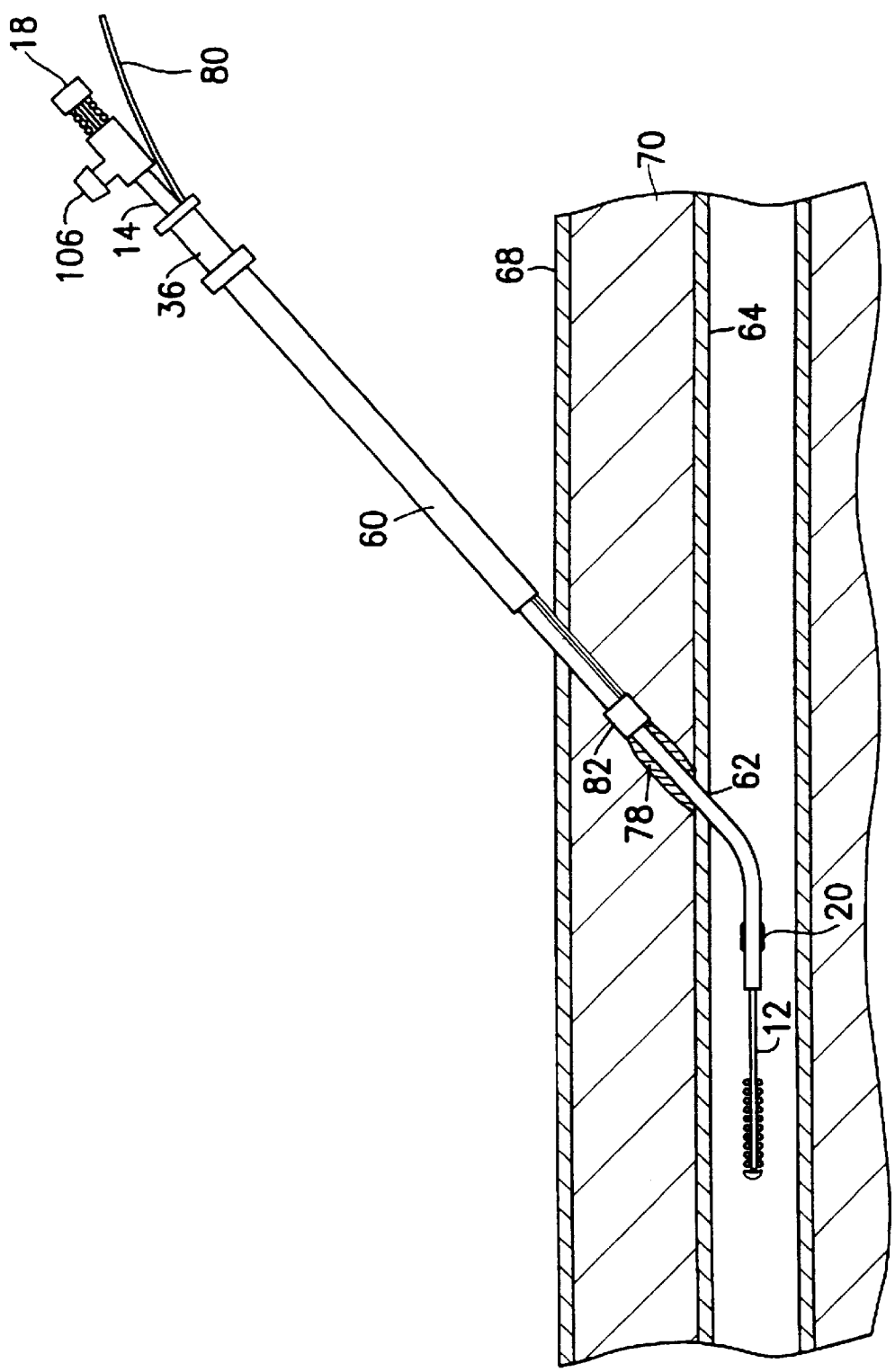
FIG. 13 shows the device of FIG. 12 wherein the anchoring wire has been retracted.

FIG. 12 is similar to FIG. 9 except that in FIG. 12 the introducer sheath 60 has been withdrawn to a position above the skin line 68. Thus, the device 100 is still anchored in place at the puncture site 62 while the plunger 80, received around the device 100, has positioned the plug of hemostatic sealing material 78 onto the puncture 62. Those skilled in the art will understand that, as a plug of sealing material 78, such as collagen, absorbs moisture from the body, it will expand to more effectively seal the puncture 62 and to reseal the hole in the center of the plug through which the device 100 is withdrawn. Thereafter, as shown in FIG. 13, the occluding balloon 20 is deflated and the inner tubular body 12 is advanced distally relative to the outer tubular body 14 so that the anchoring member 22 is retracted through opening 26 into the outer tubular member 14. The device 100 then removed from the patient's body through the center of the plug of hemostatic sealing material 78, as shown in FIG. 14, while the plunger 80 maintains the hemostatic sealing material 78 in the correct position onto the puncture 62. In the final step of the process, shown in FIG. 15, the plunger 80 has been withdrawn and the plug of hemostatic sealing material 78 is left in place to seal the puncture 62.

Figure 16:
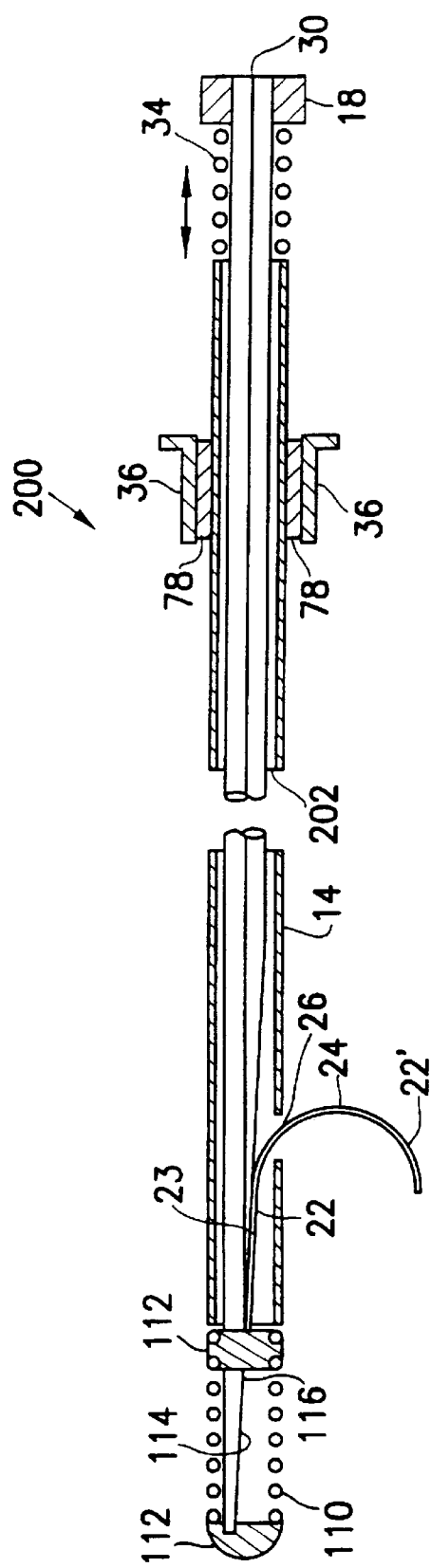
FIG. 16 shows a cross-sectional side view of a device according to a third embodiment of the present invention.

A device 200 according to a third embodiment of the invention, shown in FIG. 16, is similar to the device 100 except that it does not include an occluding balloon 20 and the outer tubular body 14 need only include a single lumen 202. In addition, the inner tubular body 12 of the device 200 need not include an interior lumen.

The operation of the device 200 is similar to the operation of the device 100 except that, instead of inflating an occluding balloon to prevent bleeding during the sealing of the puncture, manual pressure may need to be applied.

Figure 17:
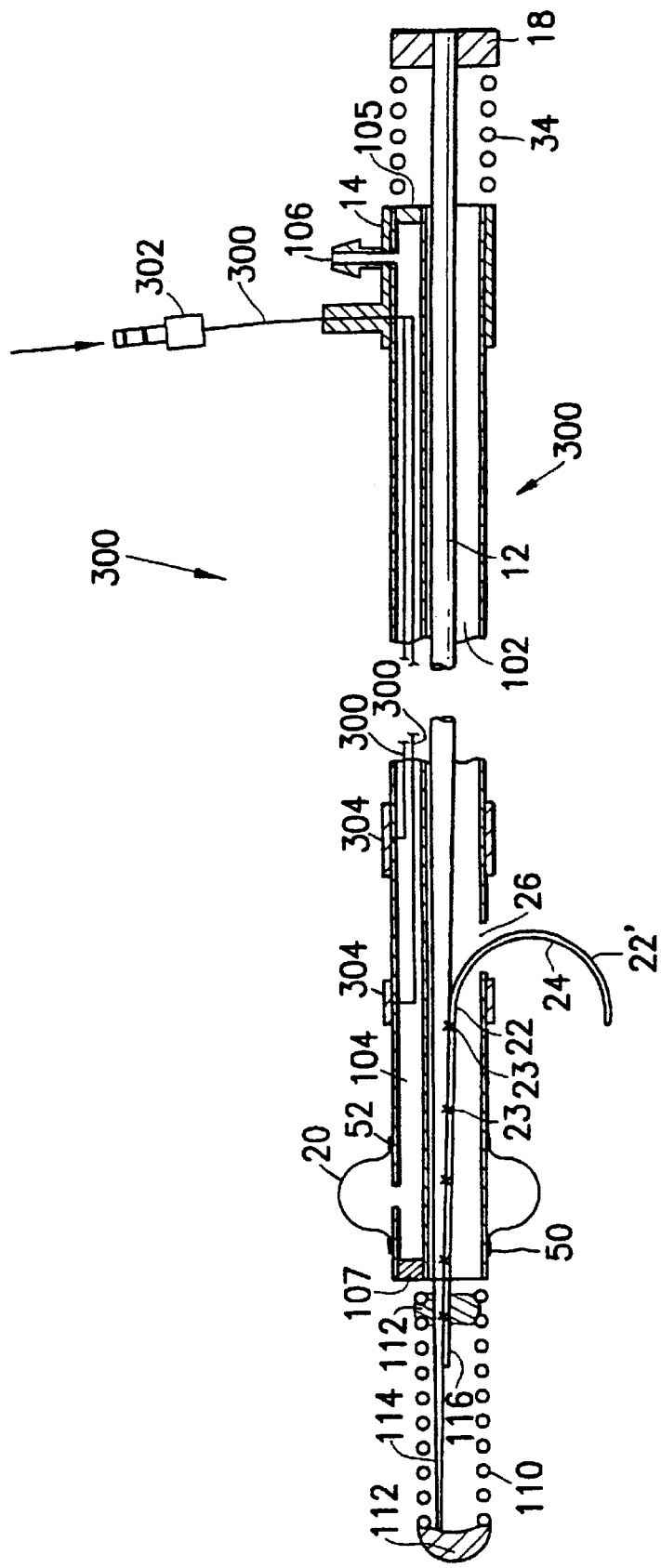
FIG. 17 shows a cross-sectional side view of a device according to a fourth embodiment of the present invention.

As shown in FIG. 17, a device 300 according to a fourth embodiment of the present invention may omit collagen plugs as discussed above, and may instead be coupled to an RF generator (not shown) by means of an electric connector 302 and leads 300. The leads 300 are coupled to electrodes 304 which, when the device is positioned properly as described above in regard to the device 100, are located on either side of the blood vessel wall 64. The electrodes 304 alternatively be movably coupled to the outer tubular body 14 so that their position relative to the anchoring member 22 may be adjusted. Thus, instead of the insertion of hemostatic sealing material 78, electricity supplied by the RF generator is be sent through the lead wires 300 to the electrodes 304 to cauterize the tissue adjacent to the puncture site 62 to seal the puncture site 62. Of course, those skilled in the art will recognize that a device 300 may include a single electrode 304 which, when in the operative position, is located on the proximal side of the puncture site 62. Such a single electrode 304 device 300 may seal punctures by cauterizing the tissue adjacent to the puncture site 62 on the proximal side thereof.

Figure 18:
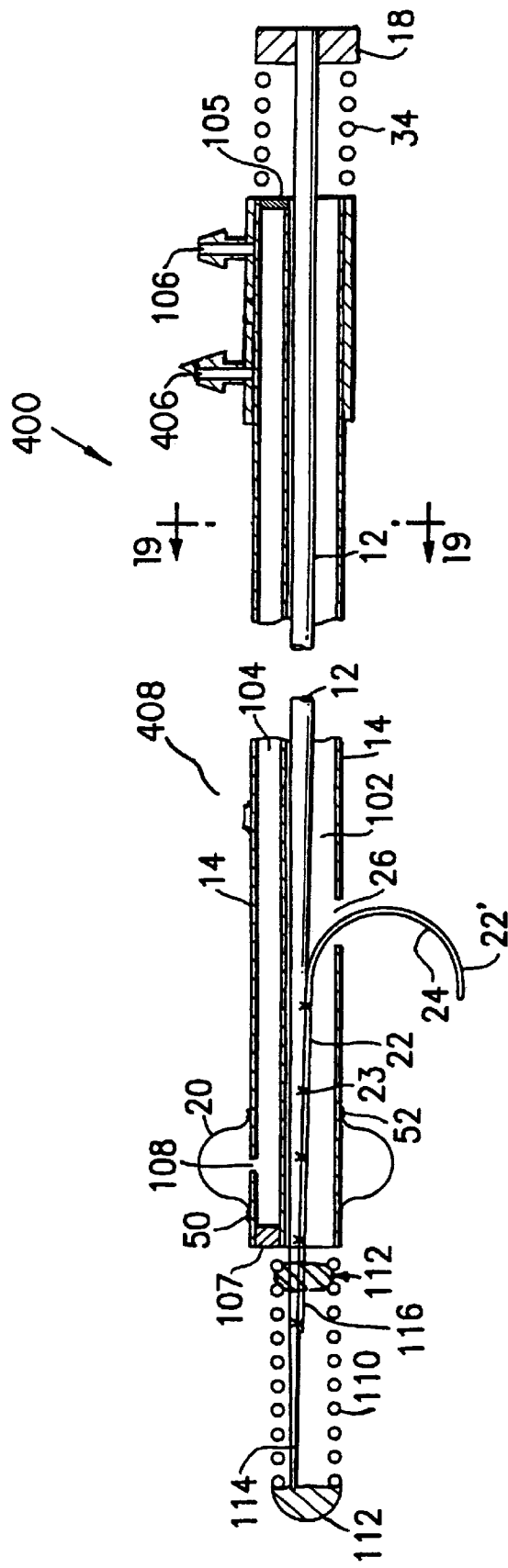
FIG. 18 is a schematic cross-sectional side view of a device according to a fifth embodiment of the present invention.

In addition to the embodiments set forth above, it is to be appreciated that various hemostatic sealing materials 78 may be substituted for the above-described collagen plugs. In addition, it should be appreciated that the sealing material 78 may be delivered to the puncture site 62 in various ways. FIG. 18 provides a schematic illustration of an exemplary device according to a fifth embodiment of the present invention, in which an adhesive material is delivered to the puncture site 62 via a lumen within the outer tubular body 14.

Specifically, FIG. 18 shows a device 400 including, in addition to several elements described above, an adhesive inlet port 406 disposed, for example, adjacent to the port 106. Adhesive inlet port 406 may, of course, be located on a different section of outer tubular body 14, but should be accessible from outside the patient's body when the device 400 is in an operative position. Adhesive inlet port 406 is adapted for connection to an adhesive source (not shown), for example an adhesive container, cartridge, tube, etc. For this purpose, adhesive inlet port 406 may include, for example, a sharpened tip capable of penetrating a seal or liner of an adhesive source, if suitable. In general, the specific configuration of adhesive inlet port 406 may vary as required by the particular shape and configuration of the adhesive source.

Adhesive inlet port 406 is in fluid communication with an adhesive lumen 404, not shown in FIG. 18. Adhesive lumen 404 extends substantially longitudinally through the outer tubular body 14, and terminates, for example, at an adhesive exit port 408. Adhesive port 408 is preferably located so that, when the device is in a desired location within a puncture to be sealed, the exit port 408 is located adjacent to the proximal side of the blood vessel wall. For purposes of clarity, adhesive exit port 408 is shown as a raised port in FIG. 18. In an alternative configuration, however, the adhesive exit port may comprise an opening in the outer tubular body 14 which is, for example, flush with the surface of outer tubular body 14.

Figure 21:
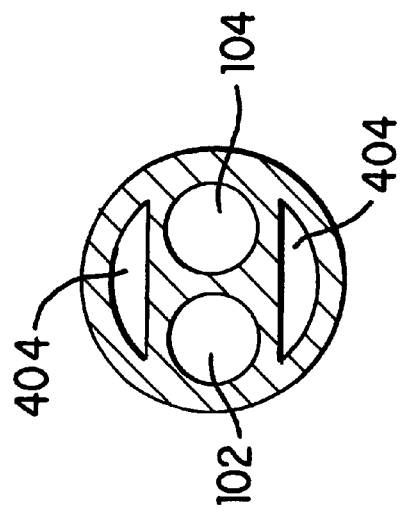
FIG. 21 is a cross-sectional view of a third exemplary lumen arrangement of the device of FIG. 18, taken along line 19—19 of FIG. 18.
Figure 20:
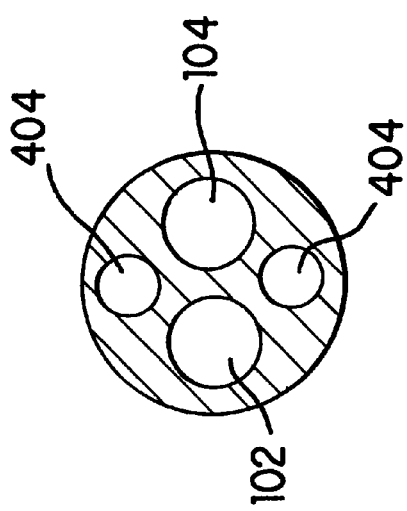
FIG. 20 is a cross-sectional view of a second exemplary lumen arrangement of the device of FIG. 18, taken along line 19—19 of FIG. 18.
Figure 19:
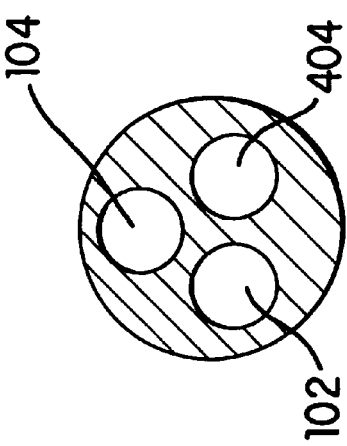
FIG. 19 is a cross-sectional view of an exemplary lumen arrangement of the device of FIG. 18, taken along line 19—19 of FIG. 18.
Figure 22:
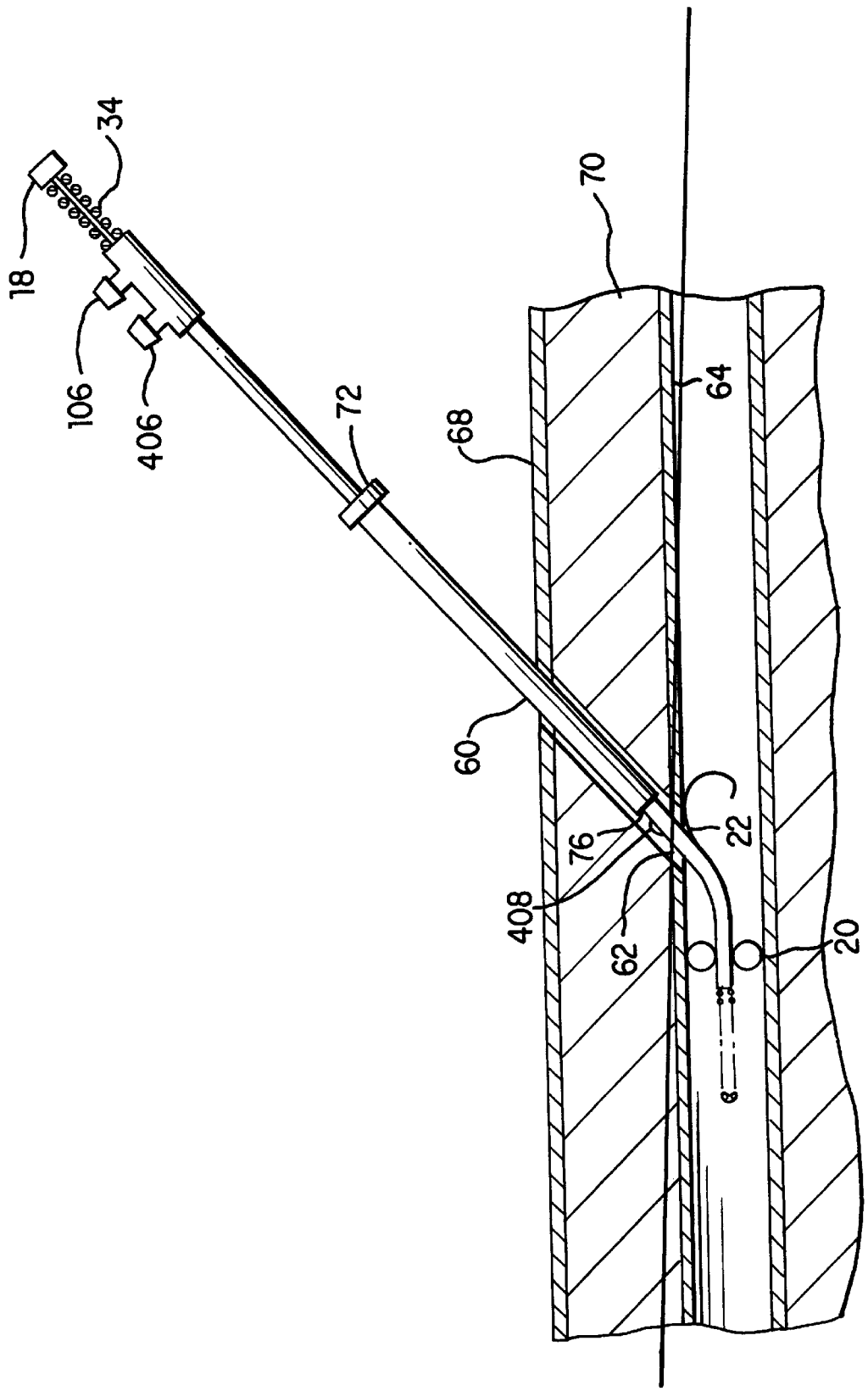
FIG. 22 is a side view of a device according to the fifth embodiment of the present invention in an operative position within a patient's body.

FIGS. 19, 20, and 21 illustrate several exemplary arrangements of the adhesive lumen 404, first lumen 102 and second lumen 104. In the embodiment of FIG. 19, a single adhesive lumen 404 is provided. In each of the embodiments of FIGS. 20 and 21, multiple adhesive lumens 404 are provided. In the latter two embodiments, each adhesive lumen 404 may terminate, for example, at a corresponding one of a plurality of adhesive exit ports 408. The adhesive exit ports 408 may be distributed, for example, about the circumference of the outer tubular body 14 to more thoroughly distribute the adhesive. Further, in the embodiment of FIG. 21, each of the adhesive lumens 404 is provided, for example, with a substantially crescent-shaped cross-section. The wider, circular first and second lumens 102 and 104 are located, for example, between two relatively long and thin adhesive lumens 404. This arrangement provides, for example, an outer tubular body with relatively thick walls compared to other embodiments.

Figure 23:
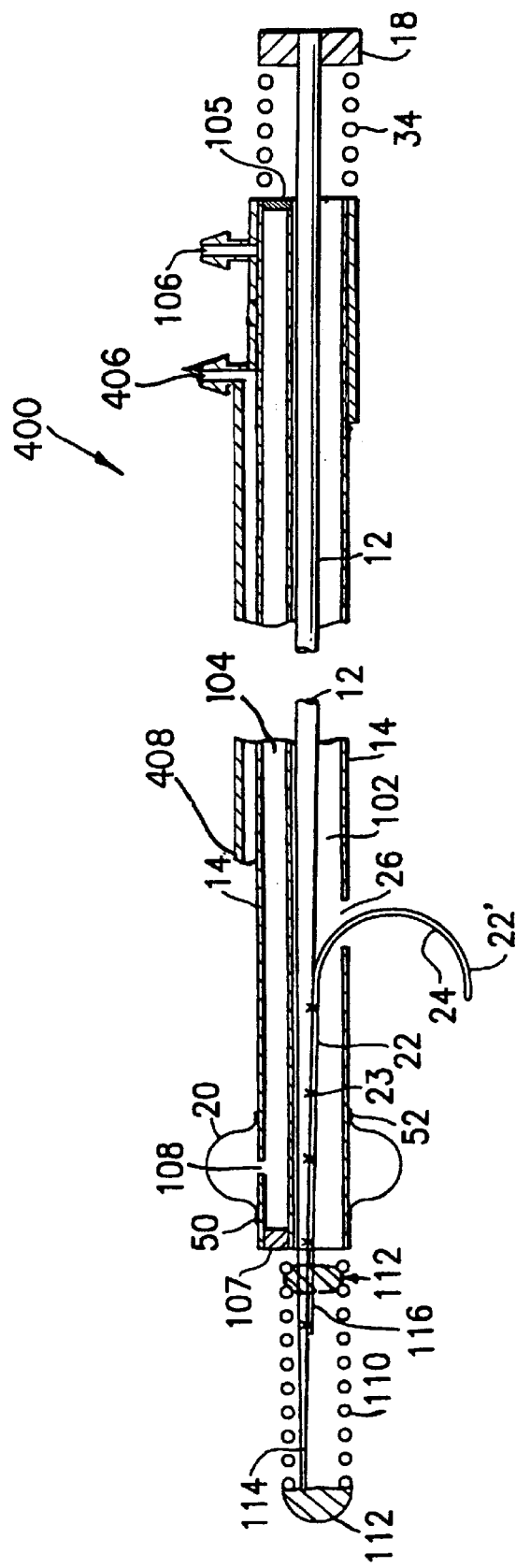
FIG. 23 is a schematic cross-sectional side view of a device according to a sixth exemplary embodiment of the present invention.

It is also possible to include an adhesive lumen 404 which runs along an outer surface of the outer tubular body 14, as illustrated in FIG. 23. In this embodiment, the cross-section of the outer tubular body (including the adhesive lumen 404) may be, for example, oval or oblong in shape as opposed to the circular cross-section of the previously described embodiments. The adhesive lumen extends along the outer surface of the tubular body 14 to an adhesive exit port 408 which faces radially outward from the tubular housing 14. Those skilled in the art will recognize that the adhesive exit port 408 may alternatively face distally rather than radially outward and any number of outward-facing exit ports or distally facing exit ports, may be provided around the circumference of the tubular housing 14.

Figure 24:
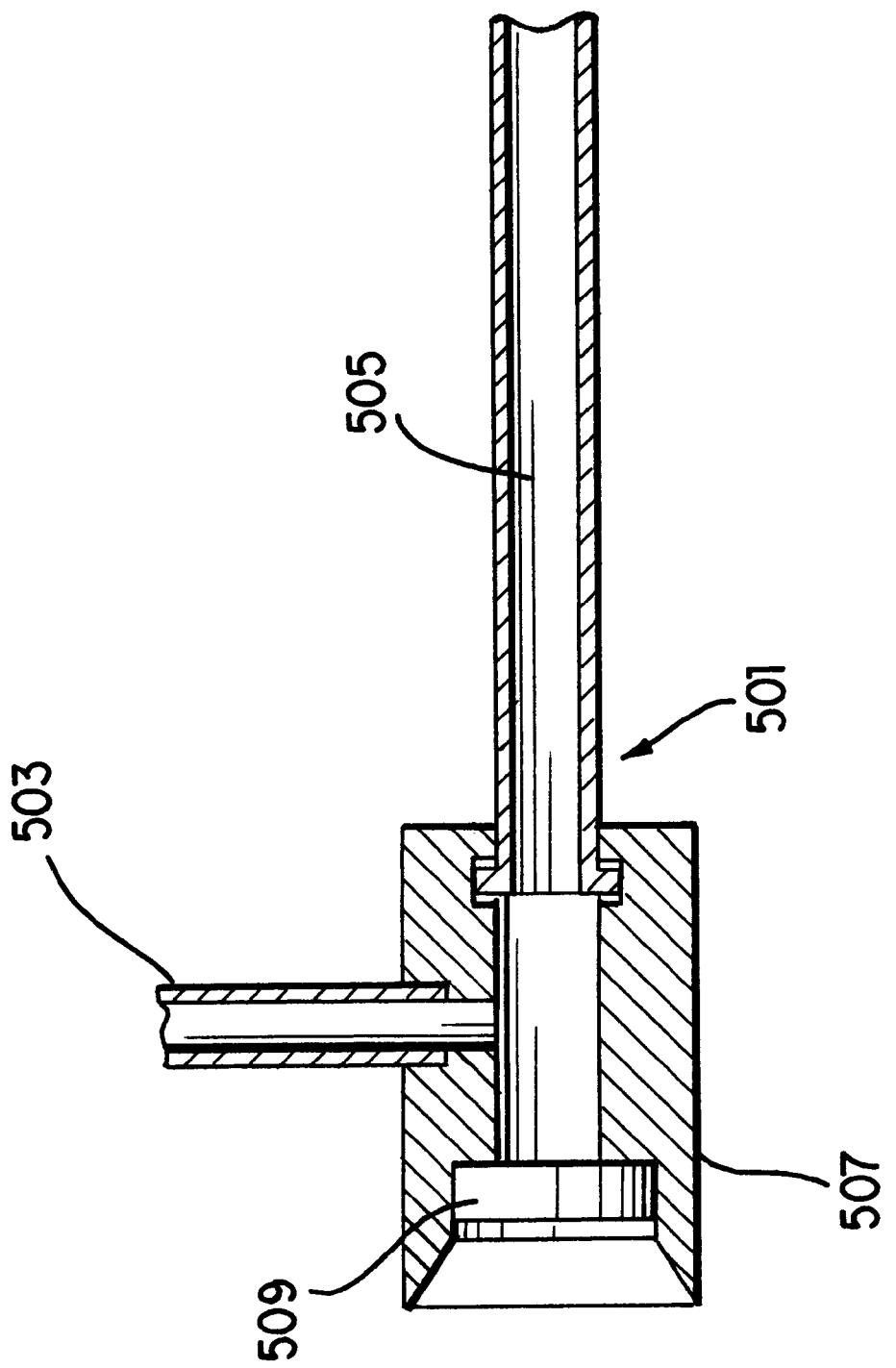
FIG. 24 is a schematic cross-sectional side view of an exemplary embodiment of an introducer sheath according to the present invention.

As shown in FIG. 24, an adhesive may be applied through an introducer sheath used in conjunction with a device 400. Specifically, a side port 503 may be provided in an introducer sheath 501 used with a device 400 according to the present invention. Introducer sheath 501 may include, for example, a sheath hub 507 having a valve 509. Introducer sheath 501 also includes an introducer lumen 505, which may have an inner diameter which is wider than an outer diameter of device 400. In this case, adhesive may be passed directly through port 503 and through introducer lumen 505 while device 400 is still within introducer sheath 501. Because device 400 is properly located as described above, the adhesive may be applied to the correct location without further positioning. In this arrangement, introducer lumen 501 acts as the adhesive lumen 404 of above-described arrangements.

A variety of adhesives may be employed in conjunction with a device according to the fifth exemplary embodiment of the present invention, and in general any suitable biocompatible adhesive may be used. Specifically, cynoacrylate and fibrin are particularly effective adhesives for use with a device according to the present invention.

A method of using a device according to the fifth exemplary embodiment of the present invention is similar to methods described above. However, in this case the step of supplying a sealing material 78 to the puncture includes applying an adhesive to the puncture via the adhesive lumen 404.

Figure 25:
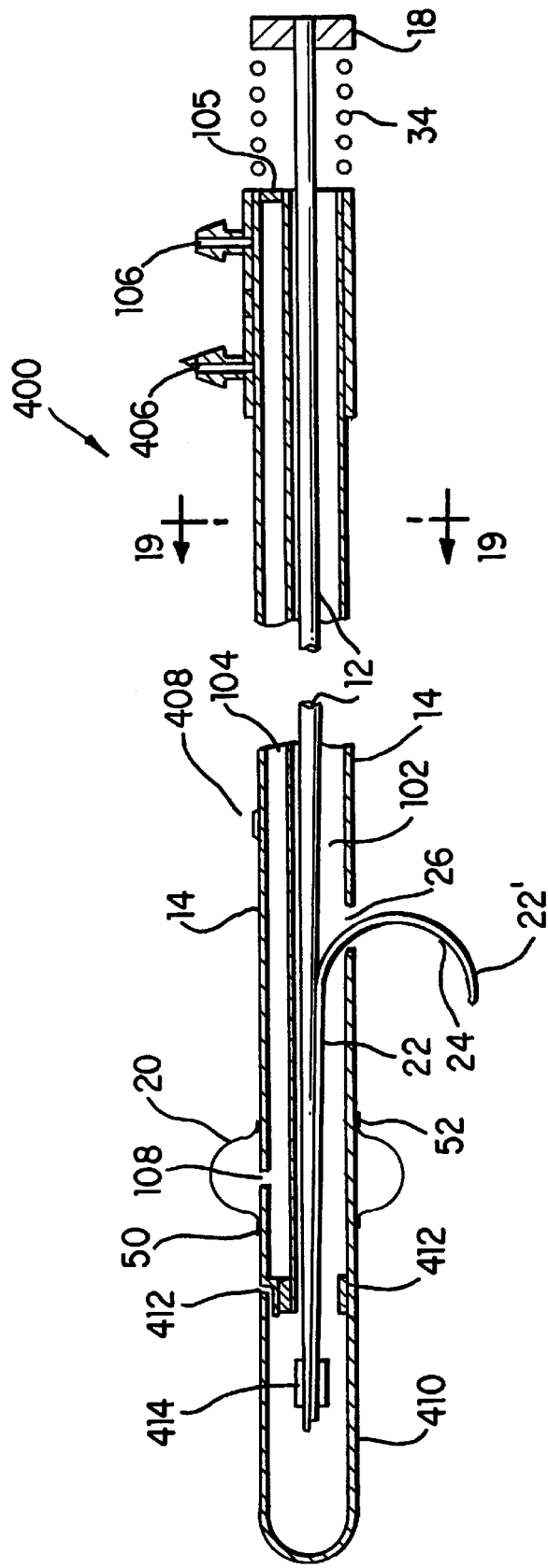
FIG. 25 shows a cross-sectional side view of a device according to a seventh embodiment of the present invention.

As shown in FIG. 25, a device 400 may also include a distal end formed as a single lumen, flexible tube 410 which may be attached to the tubular body 14 by thermal bonding or through the use of adhesive at the proximal end 412 thereof. Flexible tube 410 may assist in protecting anchoring member 22 and inner tubular body 12. In addition, the anchoring member 22 may be coupled to inner tubular body 12 by one or more plastic or metal sleeves 414 glued or crimped thereabout. Sleeves 414 may be utilized in conjunction with or as an alternative to welds 23.

While all of the embodiments of the present invention have been illustrated and described above, it will be obvious to those skilled in the art that various changes and modifications may be made thereto without departing from the scope of the invention which is intended to be limited only by the following claims. Of course, those skilled in the art will understand that, although the invention is described for sealing punctures in arteries, the devices according to each of the embodiments may be employed to seal punctures in the walls of any blood vessels or internal organs.

What we claim is:

1. A device for sealing a puncture in a blood vessel wall within a living body, comprising:

a flexible tube including an opening, wherein the flexible tube extends from a proximal end which, when the device is in an operative position, is located outside the living body, to a distal end which, in the operative position, is located within the living body on a distal side of the puncture;

an inner member slidably received within the flexible tube so that the inner member may be moved proximally and distally with respect to the flexible tube;

an adhesive channel extending from an adhesive inlet port to an adhesive exit port, the adhesive inlet port being outside the living body when the device is in the operative position and the adhesive exit port being adjacent to the puncture when the device is in the operative position; and a discrete flexible anchor member a first end of which is coupled to the inner member so that, when the inner member and the first end of the anchor member are moved with respect to the outer member, a second end of the anchor member moves between a first position in which it is received within the flexible tube and a second position in which it extends through the opening outside the flexible tube.

2. The device according to claim 1, further comprising a seal spaced distally from the anchor member for engaging tissue on a distal side of the puncture to temporarily prevent a flow of liquid to the puncture site.

3. The device according to claim 2, wherein the seal includes an occluding balloon coupled around a portion of the outside of the flexible tube distally of the opening.

4. The device according to claim 3, wherein an inflation channel extends through the inner member from a proximal end thereof to a distal end thereof so that a user may introduce fluid into and release fluid from the channel to selectively inflate and deflate the occluding balloon.

5. The device according to claim 3, wherein the flexible tube includes a first inflation lumen providing fluid communication between the occluding balloon and a proximal outlet and a second lumen in which the inner member and the anchor member are received.

6. The device according to claim 1, wherein the diameter of a distal portion of the flexible tube is reduced with respect to a proximal portion thereof and wherein the inner member includes an abutting surface for contacting an inner surface of the reduced diameter portion of the flexible tube to prevent the motion of the of the inner member, relative to the flexible tube, past a distal most position.

7. The device according to claim 6, wherein, when the inner member is in the distal most position, the flexible anchor member is entirely received within the flexible tube.

8. The device according to claim 1, wherein, when in an unstressed state, a first substantially straight portion of the flexible anchor member extends from the first end thereof substantially parallel to the inner member, to a second portion which is curved so that the second end of the flexible anchor member extends toward the distal end of the flexible tube.

9. The device according to claim 1, wherein in an unstressed state, a first portion of the flexible tube is substantially straight and wherein the distal end of the flexible tube is curved.

10. The device according to claim 1, wherein a spring is received between the flexible tube and the inner member so that the inner member is biased distally with respect to the flexible tube.

11. The device according to claim 1, wherein the adhesive lumen includes a plurality of adhesive lumens and the adhesive exit port includes a plurality of adhesive exit ports, each of the plurality of adhesive lumens terminating at a respective one of the plurality of adhesive exit ports.

12. The device according to claim 11, wherein the plurality of adhesive exit ports are distributed about the circumference of the flexible tube.

13. The device according to claim 1, wherein the adhesive lumen extends within the flexible tube.

14. A method of sealing a puncture in a tissue within a living body, comprising the steps of:

inserting a puncture sealing device into a living body so that a proximal end of the device remains outside the body while a distal portion of the device penetrates through a puncture formed in a tissue within the body so that a distal end of the device is located within a body cavity bounded by the tissue;

expanding a seal radially outwardly from the device to prevent the flow of bodily fluids to the puncture, wherein the seal is spaced distally from the anchor member;

extending an anchor member radially outwardly from the device from an insertion/retraction position into an anchor position;

partially withdrawing the device proximally from the body until the anchor member contacts the tissue of the body cavity adjacent to the puncture to locate the device in a desired position relative to the puncture;

applying an adhesive to the puncture via an adhesive lumen extending from an adhesive inlet port to an adhesive exit port;

returning the seal to its pre-expansion position;

retracting the anchor member into the insertion/retraction position; and withdrawing the device from the body through the sealing material while maintaining the sealing material in place to seal the puncture.

15. The method according to claim 14, wherein the body cavity is a blood vessel, the tissue is a blood vessel wall and the adhesive includes cynoacrylate.

16. The method according to claim 15, wherein the device includes an outer flexible tube and, wherein when the anchor member is in the insertion/retraction position, the anchor member is received within the outer flexible tube and when the anchor member is in the anchor position, it extends through an opening in the flexible tube.

17. The method according to claim 15, wherein the device includes an inner tube slidably received within the outer flexible tube and wherein the seal is an occluding balloon, and wherein the seal is expanded by supplying fluid to the occluding balloon via the inner tube to inflate the balloon.

18. The method according to claim 14, wherein the body cavity is a blood vessel, the tissue is a blood vessel wall and the adhesive includes fibrin.

19. The method according to claim 18, wherein the device includes an outer flexible tube and, wherein when the anchor member is in the insertion/retraction position, the anchor member is received within the outer flexible tube and when the anchor member is in the anchor position, it extends through an opening in the flexible tube.

20. The method according to claim 18, wherein the device includes an inner tube slidably received within the outer flexible tube and wherein the seal is an occluding balloon, and wherein the seal is expanded by supplying fluid to the occluding balloon via the inner tube to inflate the balloon.

21. The method according to claim 14, wherein the adhesive lumen includes a plurality of adhesive lumens and the adhesive exit port includes a plurality of adhesive exit ports, each of the plurality of adhesive lumens terminating at a respective one of the plurality of adhesive exit ports.

22. The method according to claim 21, wherein the body cavity is a blood vessel, the tissue is a blood vessel wall and the adhesive includes cynoacrylate.

23. The method according to claim 21, wherein the body cavity is a blood vessel, the tissue is a blood vessel wall and the adhesive includes fibrin.

24. The method according to claim 14, wherein the adhesive lumen extends through the device.

25. The method according to claim 14, the puncture sealing device is inserted into the body via an introducer sheath having an introducer lumen and wherein the adhesive lumen is the introducer lumen.

26. A device for sealing a puncture in a tissue within a living body, comprising:

a flexible tube including an opening, wherein the flexible tube extends from a proximal end which, when the device is in an operative position, is located outside the living body, to a distal end which, in the operative position, is located within the living body on a distal side of the puncture;

an inner member slidably received within the flexible tube so that the inner member may be moved proximally and distally with respect to the flexible tube;

an adhesive lumen extending through the flexible tube from an adhesive inlet port to an adhesive exit port, the adhesive inlet port being outside the living body when the device is in the operative position and the adhesive exit port being adjacent to the puncture when the device is in the operative position; and a flexible anchor member a first end of which is coupled to the inner member so that, when the inner member is moved with respect to the outer member, a second end of the anchor member moves between a first position in which it is received within the flexible tube and a second position in which it extends through the opening outside the flexible tube, wherein, when in an unstressed state, a first substantially straight portion of the flexible anchor member extends from the first end thereof substantially parallel to the inner member, to a second portion which is curved so that the second end of the flexible anchor member extends toward the distal end of the flexible tube.

\* \* \* \* \*